United States Patent

Hayashi et al.

[11] 4,182,878
[45] Jan. 8, 1980

[54] 1-PHENYL-1H-PYRAZOLO[3,4-d]PYRIMIDINE-4-CARBONITRILE AND A METHOD FOR ITS PREPARATION

[75] Inventors: Eisaku Hayashi; Takeo Higashino; Shin-ichi Suzuki, all of Shizuoka, Japan

[73] Assignee: The Lion Dentrifice Co., Ltd., Tokyo, Japan

[21] Appl. No.: 893,527

[22] Filed: Apr. 4, 1978

[30] Foreign Application Priority Data

Aug. 27, 1977 [JP] Japan ................. 52/103022

[51] Int. Cl.² ................. A61K 31/415; A61K 31/505; C07D 487/04
[52] U.S. Cl. ................. 544/262; 424/251
[58] Field of Search ................. 544/262

[56] References Cited

U.S. PATENT DOCUMENTS 2,965,643  12/1960  Druey et al. ............ 544/262
3,187,006  6/1965  Druey et al. ............ 544/262

Primary Examiner—Donald G. Daus
Assistant Examiner—James H. Turnipseed
Attorney, Agent, or Firm—Toren, McGeady and Stanger

[57] ABSTRACT

Novel derivatives of 1-phenyl-1H-pyrazolo[3,4-d]pyrimidine substituted at the 4-position of the pyrimidine ring are provided. A typical example is 1-phenyl-1H-pyrazolo[3,4-d]pyrimidine-4-carbonitrile. The compounds exhibit excellent anti-carcinogenic activities as evidenced by the animal test with mice.

2 Claims, 2 Drawing Figures

1-PHENYL-1H-PYRAZOLO[3,4-d]PYRIMIDINE-4-CARBONITRILE AND A METHOD FOR ITS PREPARATION

BACKGROUND OF THE INVENTION

The present invention relates to novel pyrimidine derivatives useful as carcinostatic substances. More particularly, the invention relates to 1-phenyl-1H-pyrazolo[3,4-d]pyrimidine-4-carbonitrile and a method for its preparation.

In recent years, a number of carcinostatic substances for use in chemotherapy against cancers have been developed and proposed. Among others, various derivatives of pyrimidine or purine are known to have anti-carcinogenic activites and antagonize the pyrimidine or purine metabolism pertaining to nucleic acid synthesis. However, the use of these carcinostatic substances has thus far served merely as a measure auxiliary in conjunction with surgical operations to resect cancer cells and their peripheral tissues, or radiotherapy to destroy cancer cells.

The local cancer cells, though resected by surgical operations, are within the bounds of possibility of metastasizing to other parts of the body and, once such metastasis has taken place throughout the body, a complete cure of the cancer will hardly be expected by the local resection. Therefore, the general and main therapeutic means to cure cancers is chemotherapy whereby the growth of the cancer cells is prevented by the action of suitable carcinostatic substances. For the purpose, the development of substances having excellent anti-carcinogenic activities and useful in the chemotherapy of cancers has been eagerly desired.

SUMMARY OF THE INVENTION

It is therefore the object of the present invention to provide novel carcinostatic substances which are suitable for use in the chemotherapy of cancers.

The present invention has been completed by the discovery that a novel substance 1-phenyl-1H-pyrazolo[3,4-d]pyrimidine-4-carbonitrile expressed by the structural formula

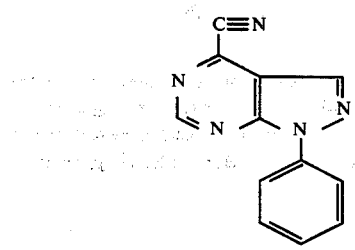

can be prepared from 4-chloro-1-phenyl-1H-pyrazolo[3,4-d]pyrimidine compounds and that this substance has an excellent anti-carcinogenic activity, and further that its derivatives in which the substituent group at the 4-position is either

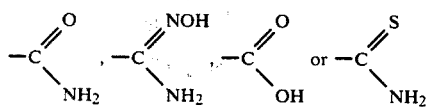

have a similar anti-carcinogenic activity.

DETAILED DESCRIPTION OF THE PREFERRED EMBODIMENTS

Figure 1:
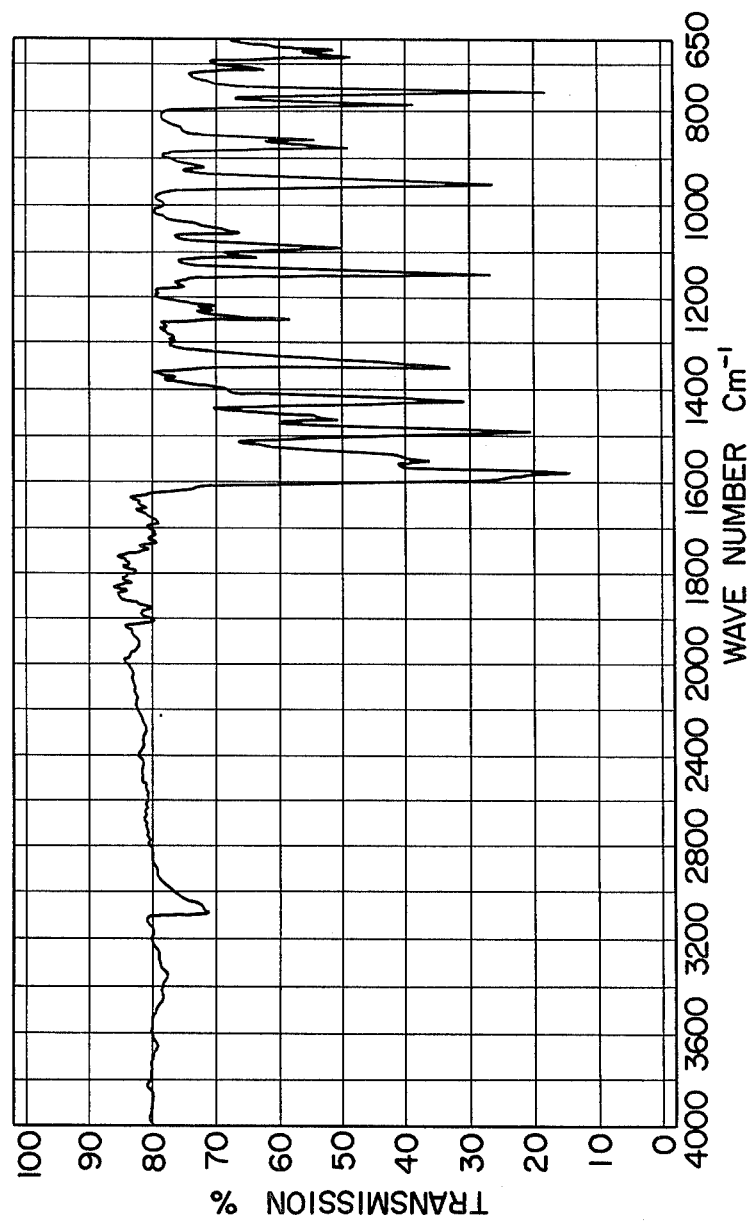
FIG. 1 shows an infrared absorption spectrum of 1-phenyl-1H-pyrazolo[3,4-d]pyrimidine-4-carbonitrile.

The inventive compound, 1-phenyl-1H-pyrazolo[3,4-d]pyrimidine-4-carbonitrile (hereinafter referred to as Compound I) expressed by the structural formula

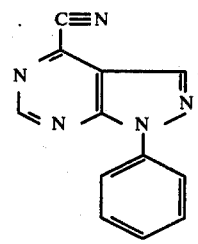

is obtained in the form of colorless cubic crystals as precipitated from a benzene solution, and has a melting point of 190.5°–191.5° C.

Compound I exhibits activities to retard cell multiplication. Its $LD_{50}$ value is 100 mg/kg in mouse by oral administration. This compound is stable, and can be readily processed into dosage forms by a conventional means to be useful for chemotherapy as a carcinostatic substance.

Compound I can be synthesized at a high yield, as an example, by reacting 4-chloro-1-phenyl-1H-pyrazolo[3,4-d]pyrimidine (hereinafter referred to as Compound II) with an alkali cyanide, such as, potassium cyanide or sodium cyanide in an amount, for example, equivalent to 2 to 5 times by mole in a solvent, such as, dimethylsulfoxide and dimethylformamide as shown in the under-mentioned reaction scheme (Route A). As a further example, Compound II is reacted with a sulfinate, such as sodium p-toluenesulfinate, in a solvent, such as dimethylsulfoxide and dimethylformamide, to produce 4-sulfonyl-1-phenyl-1H-pyrazolo[3,4-d]pyrimidine (hereinafter referred to as Compound III), and Compound III thus produced is reacted with an alkali cyanide, such as potassium cyanide or sodium cyanide, to form Compound I as shown in the reaction scheme (Route B).

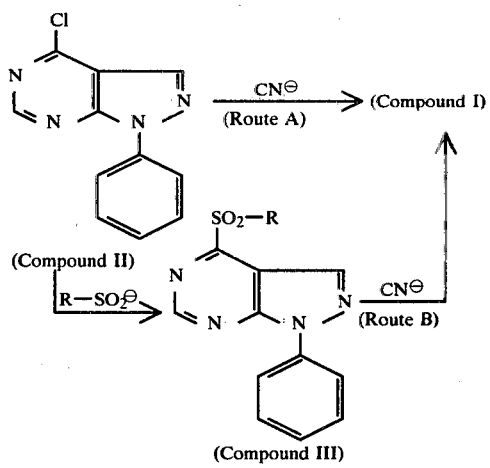

In the above reaction scheme, R is a lower alkyl, e.g. methyl group and ethyl group, or an aromatic group, e.g. phenyl group and p-methylphenyl group.

Whereas the reaction conditions in both Route A and Route B are almost identical with respect to reaction temperature, i.e., from room temperature to about 50° C. and reaction time, i.e., from 0.5 to 2 hours, Route A is advantageous over Route B because of its simple single step reaction, despite a difficulty in the separation of any unreacted Compound II from the Compound I product. The method of Route B, on the other hand, has no problem in such separation because any unreacted Compound III can be readily converted, by reaction with an alkali, to a 4-OH derivative (equivalent to the under-mentioned Compound V), which is then readily separated from the product by use of the solvent treatment technique.

Several novel pyrimidine compounds can be derived from Compound I. For example, by subjecting Compound I to hydrolysis reaction with concentrated sulfuric acid, 1-phenyl-1H-pyrazolo[3,4-d]pyrimidine-4-carboxamide (hereinafter referred to as Compound IV). As a further example, Compound IV can be prepared by reacting Compound I with an aqueous solution of hydrogen peroxide and potassium carbonate. These reaction schemes are shown below.

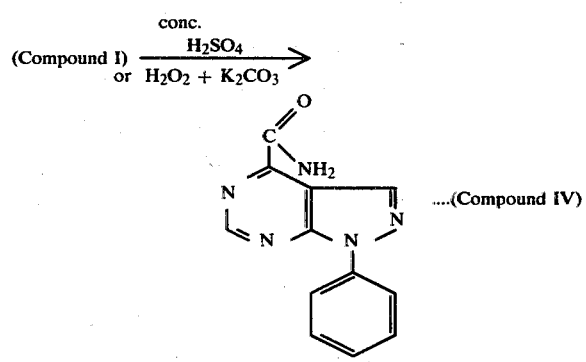

Some other examples are provided in the following.

Hydrolysis of Compound I with a 10% aqueous solution of sodium hydroxide produces 4-hydroxy-1-phenyl-1H-pyrazolo[3,4-d]pyrimidine (hereinafter referred to as Compound V).

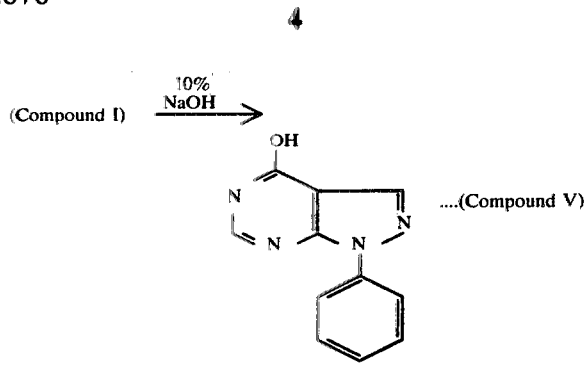

Reaction of Compound I with hydroxylamine produces 1-phenyl-1H-pyrazolo[3,4-d]pyrimidine-4-carboxamidoxime (hereinafter referred to as Compound VI), while the reaction with hydrazine produces 4-hydrazino-1-phenyl-1H-pyrazolo[3,4-d]pyrimidine (hereinafter referred to as Compound VII), as a result of the substitution of the nitrile group in Compound I, as shown in the following reaction schemes.

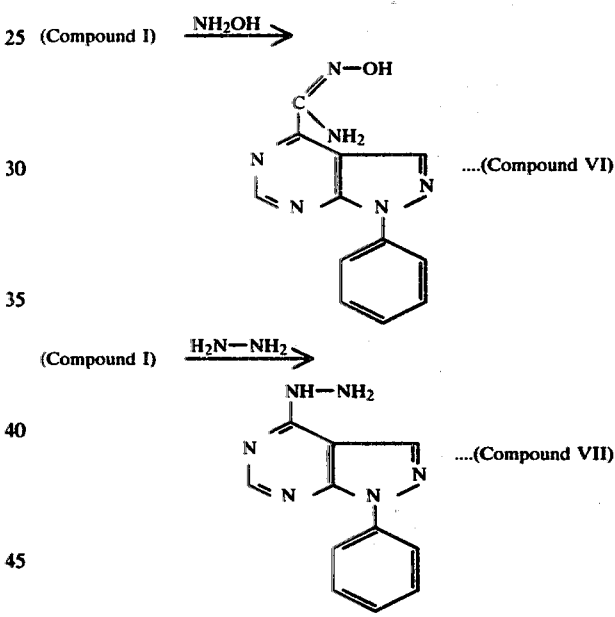

Reaction of Compound I with a primary amine $RNH_2$ where R is an alkyl group or an aryl group produces a compound (Compound VIII) represented by the general formula given in the following reaction scheme.

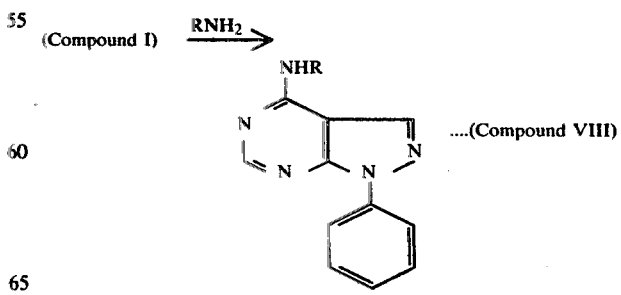

Reaction of Compound I with a carbanion, such as active methylene compounds and ketones, in the presence of sodium amide in dimethylformamide produces a compound (Compound IX) represented by the general formula where X and Y are each a carbonyl group, an alkyl group, an aryl group, a cyano group, an ester group, or a hydrogen atom, as given in the following reaction scheme.

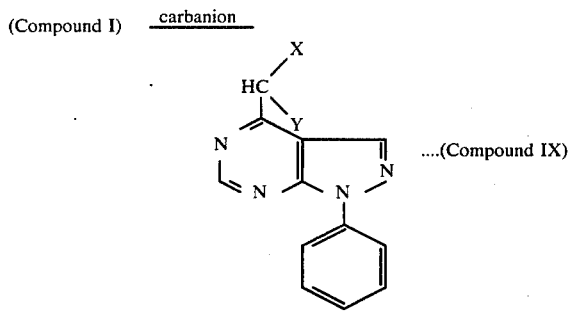

Hydrolysis reaction of Compound I with diluted sulfuric acid or hydrochloric acid produces 1-phenyl-1H-pyrazolo[3,4-d]pyrimidine-4-carboxylic acid (hereinafter referred to as Compound X), while a reaction with hydrogen sulfide results to produce 1-phenyl-1H-pyrazolo[3,4-d]pyrimidine-4-thiocarboxamide (hereinafter referred to as Compound XI), as shown in the following reaction schemes.

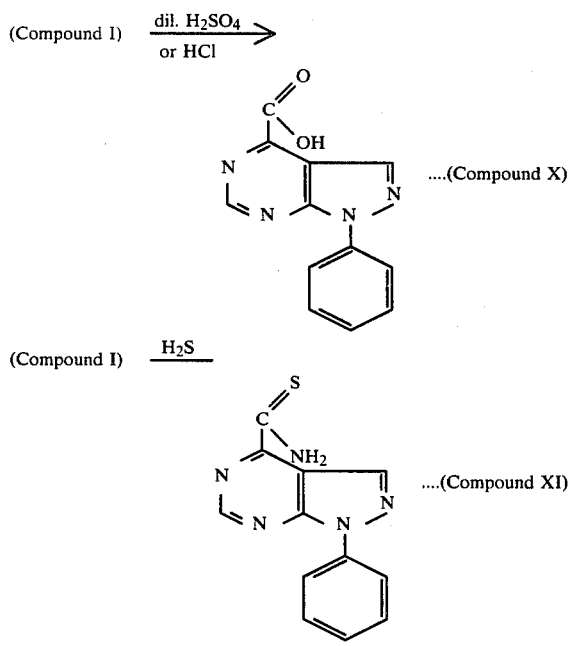

Compounds IV, VI, X and XI are all novel compounds, having anti-carcinogenic activities. Thus Compound I is useful as the intermediate material for the preparation of these novel compounds. In addition, Compound I can serve as the intermediate material for the preparation of known Compounds V, VII, VIII and IX, the processes of which are novel.

In the following, examples of the processes for the preparation of Compounds I, IV, VI, X and XI and the properties of those compounds by which to be identified from each other are given.

Process 1 (Preparation of Compound I—Route A)

A solution prepared by dissolving 10 g of Compound II and 10 g of potassium cyanide in 400 ml of dimethylsulfoxide (hereinafter referred to as DMSO for brevity) was agitated for about 1.5 hours at 40° C. during which reaction took place. Then the resulting solution was poured over 400 g of ice blocks, followed by extraction with chloroform. The chloroform extract thus obtained was dried by use of anhydrous sodium sulfate and evaporated to dryness, and the residue was re-dissolved in 50 ml of chloroform. The chromatographic separation of this chloroform solution with 100 ml of silica gel as the adsorbent and with benzene as the eluent resulted to form 6.91 g of a reaction product in the first fraction. The product was identified as Compound I by the under-mentioned analytical data. The yield was 72.1% of the theoretical.

Appearance: colorless, cubic crystals (when precipitated from the benzene solution).

Melting point: 190.5°–191.5° C.

Results of elementary analysis: C, 65.15%; H, 3.19%; N, 31.66% (calculated as $C_{12}H_7N_5$). C, 64.87%; H, 3.46%; N, 31.54% (found).

$M^+$ in mass spectrum: 221 (molecular weight as $C_{12}H_7N_5$ 221.22).

Maxima in ultraviolet absorption spectrum in 99.5% ethanol: $\log \varepsilon$ at 250.5 nm 4.59 and at 335.0 nm 3.29.

NMR spectrum: $H_3$ or $H_6$ 9.24, 8.59.

Figure 2:
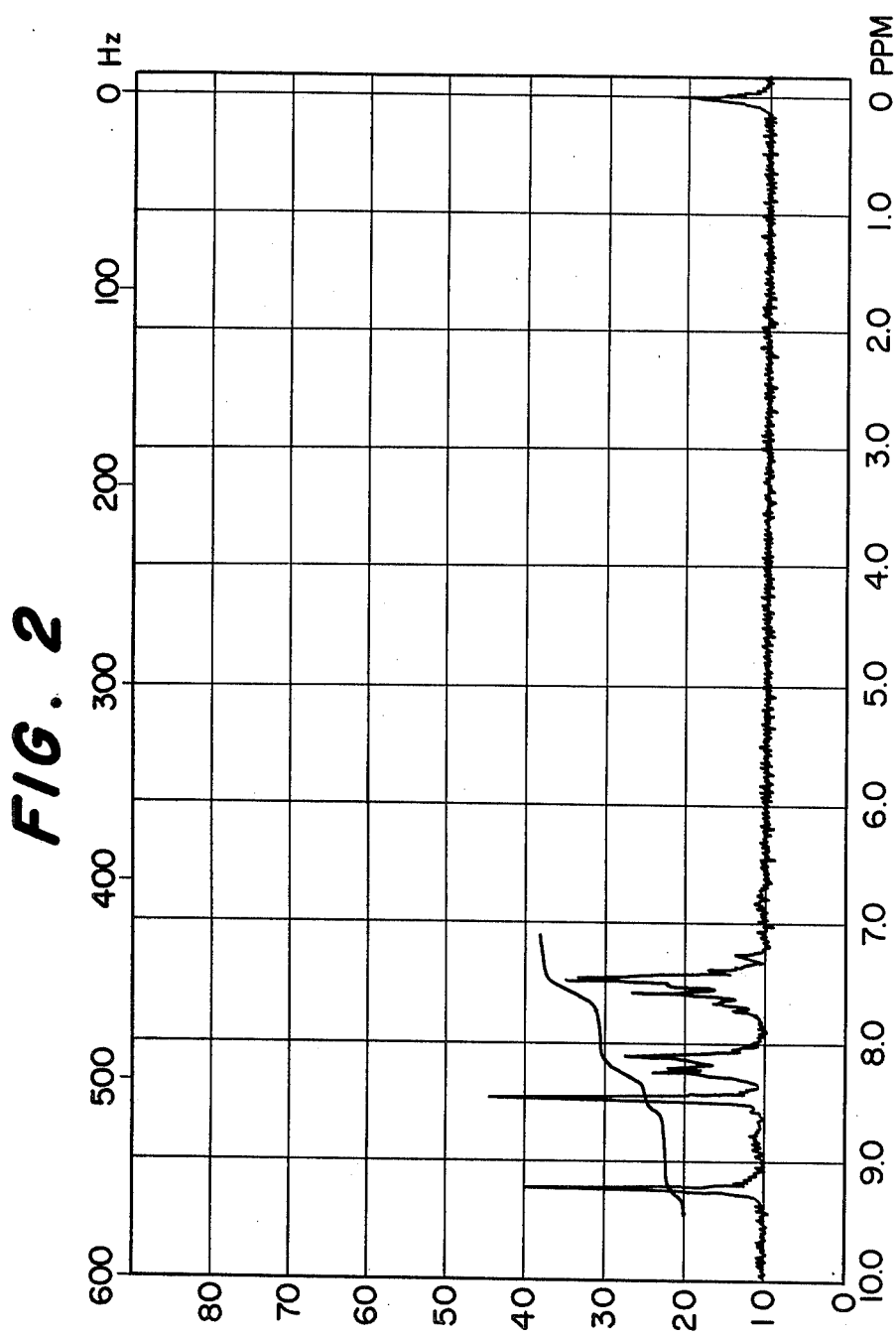
FIG. 2 shows a nuclear magnetic resonance spectrum of the same compound.

The infrared absorption spectrum and the NMR spectrum of Compound I are shown in FIGS. 1 and 2 respectively.

Process 2 (Preparation of Compound I via Compound III—Route B)

Into a solution of 3.00 g of Compound II in 60 ml of DMSO was added 3.00 g of sodium-p-toluenesulfinate, followed by agitation for about 1 hour at room temperature to effect reaction, and the resultant reaction mixture was poured into ice and water. The crystalline product there precipitated was taken by filtration and washed thoroughly with water, followed by further washing three times with small portions of cold methanol. The thus obtained product was dissolved in chloroform and concentrated after removal of undissolved matter by filtration. A crystalline product precipitated on addition of methanol was taken by filtration and recrystallized from methanol solution at a yield of 4.36 g. The analytical data of this compound are set forth below, by which the compound was identified as 4-(p-tolylsulfonyl)-1-phenyl-1H-pyrazolo[3,4-d]pyrimidine. The yield was 94.4% of the theoretical.

Appearance: colorless, needle-like crystals (when precipitated from a methanol solution).

Melting point: 196°–197° C.

Results of elementary analysis: C, 62.70%; H, 4.03%; N, 15.99% (calculated as $C_{18}H_{14}N_4O_2S$). C, 61.26%; H, 4.03%; N, 15.88% (found).

A solution of 5.0 g of the thus obtained 4-(p-tolylsulfonyl)-1-phenyl-1H-pyrazolo[3,4-d]pyrimidine and 2.0 g of potassium cyanide in 20 ml of DMSO was agitated for 30 minutes at room temperature to effect reaction. The resulting solution was poured over 300 g of ice blocks. The crystalline product there precipitated was taken by filtration, washed with water and, after drying, dissolved in 50 ml of chloroform. The solution thus formed was subjected to chromatographic separation using 100 ml of silica gel as the adsorbent and with benzene as the eluant, to give 2.6 g of a reaction product in the first fraction. The product was identified as Compound I. The yield of Compound I based on Compound III was 82.4% of the theoretical corresponding to the overall yield of 77.8% starting from Compound II.

When the same procedure except that the solvent was dimethylformamide instead of DMSO was repeated, almost the same results were obtained.

Process 3 (Preparation of Compound IV)

A solution of 5.00 g of Compound I in 40 ml of concentrated sulfuric acid was heated in a hot water bath at 90° C. for 5 minutes, and then taken out of the bath and allowed to cool for 10 minutes at room temperature. The resulting solution was poured into ice and water, and the precipitated crystalline product was taken by filtration, washed thoroughly with water and dried. Recrystallization of this dried product from a chloroform solution resulted to produce 5.21 g of a colorless crystalline product which was identified as Compound IV by the under-mentioned analytical data. The yield was 96.4% of the theoretical.

Appearance: colorless, needle-like crystals.
Melting point: 257-258° C.
Results of elementary analysis: C, 60.25%; H, 3.79%; N, 29.27% (calculated as $C_{12}H_9N_5O$). C, 59.82%; H, 3.76%; N, 29.30% (found).
$M^+$ in mass spectrum: 239 (molecular weight as $C_{12}H_9N_5O$ 239.24).
Absorption bands in infrared absorption spectrum (in KBr): 3400 $cm^{-1}$, 3280 $cm^{-1}$ and 3160 $cm^{-1}$ (assigned to >NH); 1720 $cm^{-1}$ (assigned to >C=O).
Maxima in ultraviolet absorption spectrum in 99.5% ethanol: log $\epsilon$ at 249 nm 4.45 and at 324 nm 3.24.
NMR spectrum: $H_3$ or $H_6$ 9.50, 9.36 (p.p.m., in $CF_3COOD$).

Process 4 (Preparation of Compound IV)

A solution of 5.00 g of Compound I in 100 ml of acetone was mixed with 75 ml of 30% hydrogen peroxide and 100 ml of 10% aqueous solution of potassium carbonate. The resulting mixture was heated in a water bath for about 30 minutes, while the acetone was evaporated. The crystalline product precipitated on addition of water was taken by filtration and dried with subsequent recrystallization from a chloroform solution to form 5.30 g of a product. The product was identical with Compound IV obtained in Process 3 above. The yield was 98.0% of the theoretical.

Process 5 (Preparation of Compound VI)

A solution of 7.5 g of hydroxylamine hydrochloride in 50 ml of water was mixed with 8.25 g of sodium hydrogencarbonate and, after subsidence of foaming, with 5.00 g of Compound I and 5 ml of methanol, followed by heating under reflux with agitation for about 30 minutes. The reaction mixture was then poured into ice and water, and the crystalline product there precipitated was taken by filtration, washed with water and dried with subsequent recrystallization from an acetone solution to form 5.43 g of a product. The product was identified as Compound VI by the under-mentioned analytical data. The yield was 94.5% of the theoretical.

Appearance: colorless, needle-like crystals.
Melting point: 224°-225° C.
Results of elementary analysis: C, 56.69%; H, 3.96%; N, 33.05% (calculated as $C_{12}H_{10}N_6O$). C, 56.32%; H, 3.92%; N, 33.34% (found).

$M^+$ in mass spectrum: 254 (molecular weight as $C_{12}H_{10}N_6O$ 254.25).
Absorption bands in infrared absorption spectrum (in KBr): 3450 $cm^{-1}$ (assigned to —OH); 3350 $cm^{-1}$ and 3250 $cm^{-1}$ (assigned to >NH); 1665 $cm^{-1}$ (assigned to >C=O).
Maxima in ultraviolet absorption spectrum in 99.5% ethanol: log $\epsilon$ at 245.5 nm 4.48 and at 322 nm 3.89.
NMR spectrum: $H_3$ or $H_6$ 9.13, 8.68; $NH_2$ 6.14; —OH 10.7 (p.p.m., in DMSO).

Process 6 (Preparation of Compound X)

A solution of 5.00 g of Compound I in 40 ml of 70% sulfuric acid was heated for about 1 hour in a boiling water bath and then cooled to room temperature. The crystalline product precipitated on addition of 100 ml of water was taken by filtration, washed with water and dried with subsequent recrystallization from a methanol solution to form 5.13 g of a product. The product was identified as Compound X by the under-mentioned analytical data. The yield was 92.6% of the theoretical.

Appearance: yellow, scale-like crystals.
Melting point: 169°-170° C. (with decomposition).
Results of elementary analysis: C, 60.00%; H, 3.36%; N, 23.32% (calculated as $C_{12}H_8N_4O_2$). C, 59.73%; H, 3.32%; N, 23.68% (found).
$M^+$ in mass spectrum: 240 (molecular weight as $C_{12}H_8N_4O_2$ 240.22).
Absorption bands in infrared absorption spectrum (in KBr): 1680 $cm^{-1}$ (assigned to >C=O).
Maxima in ultraviolet absorption spectrum in 99.5% ethanol: log $\epsilon$ at 250 nm 4.34 and at 317.5 nm 3.20.
NMR spectrum: $H_3$ or $H_6$ 9.30, 8.74 (p.p.m., in DMSO).

When the 70% sulfuric acid was replaced with concentrated hydrochloric acid (36% HCl), almost the same results were obtained.

Process 7 (Preparation of Compound XI)

Into a solution of 5.00 g of Compound I in 300 ml of pyridine was introduced hydrogen sulfide gas until the solution increased its weight by 5.00 g. The resulting solution was heated under reflux for about 30 minutes, followed by removal of the pyridine by distillation and washing of any residue with cold benzene, and recrystallized from a benzene solution to form 5.43 g of a product. The product was identified as Compound XI by the under-mentioned analytical data. The yield was 94.1% of the theoretical.

Appearance: reddish yellow, needle-like crystals.
Melting point: 217°-218° C.
Results of elementary analysis: C, 56.46%; H, 3.55%; N, 27.43% (calculated as $C_{12}H_9N_5S$). C, 56.31%; H, 3.54%; N, 27.70% (found).
$M^+$ in mass spectrum: 255 (molecular weight as $C_{12}H_9N_5S$ 255.30).
Absorption bands in infrared absorption spectrum (in KBr): 3300 $cm^{-1}$, 3240 $cm^{-1}$ and 3100 $cm^{-1}$ (assigned to >NH(SH)); 1635 $cm^{-1}$ (assigned to >C=S).
Maxima in ultraviolet absorption spectrum in 99.5% ethanol: log $\epsilon$ at 252 nm 4.37 and at 340 nm 3.66.
NMR spectrum (p.p.m., in DMSO): SH or NH 10.19$^{(S)}$; 10.69$^{(S)}$ $H_3$ or $H_6$ 9.17, 9.09 (p.p.m., in DMSO).

In addition to the foregoing examples of preparation processes, Compounds I, IV, VI, X and XI were evaluated with respect to their carcinostatic activities and acute toxicities by animal tests as follows.

Each of mice (ddY) having a body weight of about 25 g was subcutaneously innoculated with $3 \times 10^6$ of Ehrlich's tumor cells, and the thus inoculated mice were divided into 5 "sample" groups and 3 "control" groups, each group consisting of five or four mice. The thus treated mice belonging to the control groups were observed over a period of 14 days. On the other hand, each mouse belonging to the sample groups was given a 1 mg dose of Compounds I, IV, VI, XI or X by injection into the abdominal coelom every day during the period beginning after 24 hours from the innoculation of the tumor cells, and as indicated in the table below.

At the end of the 14-day period following the abovementioned innoculation of the tumor cells, the tumor tissues of each mouse were taken out and weighed, so that comparison could be made between the weights of the tumor tissues taken from the sample groups and the control groups. The results are set forth in the table. Further in the table, "Toxicity" is expressed by the number of mice died in the group during the 14-day period following the transplantation of the cancer cells and "Evaluation" is based on the ratios of S/C in percentages and expressed by "++" when the percentage is 0-25%, "+" when the percentage is 26-50%, and "±" when the percentage is 51-75%.

As is clear from the data in the table, Compound I of the present invention is very effective in preventing the multiplication of cancer cells and Compounds IV, VI, XI and X as the derivatives of Compound I are also effective in preventing the multiplication of cancer cells.

Table

| Compound | Dosage period, days | Toxicity, ratio of died mice | Weight of tumor tissues in the sample group, g (S) | Weight of tumor tissues in the control group, g (C) | Ratio of S/C, % | Evaluation |
| --- | --- | --- | --- | --- | --- | --- |
| I | 10 | 1/5 | 0.43 ± 0.40 | 4.44 ± 1.02 | 9.7 | ++ |
| IV | 10 | 0/5 | 3.05 ± 1.40 | | 68.7 | ± |
| XI | 7 | 0/4 | 0.63 ± 0.08 | 1.36 ± 0.15 | 46.3 | + |
| VI | 7 | 0/4 | 0.43 ± 0.15 | | 31.6 | + |
| X | 7 | 0/4 | 1.14 ± 0.27 | 1.52 ± 0.27 | 75.0 | ± |

What is claimed is:

1. A derivative of 1-phenyl-1H-pyrazolo[3,4-d]pyrimidine having the structural formula

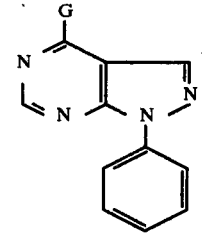

where G is a group selected from the class consisting of

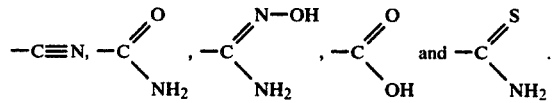

2. 1-Phenyl-1H-pyrazolo[3,4-d]pyrimidine-4-carbonitrile.

* * * * *